(12) United States Patent
Taylor, Sr.

(10) Patent No.: US 7,240,414 B2
(45) Date of Patent: Jul. 10, 2007

(54) PROSTHETIC INTERIOR CASTING PROCESS AND PRODUCT

(76) Inventor: Matthew T. Taylor, Sr., 501 Cedar Rd. Ste 2B, Chesapeake, VA (US) 23322

( * ) Notice: Subject to any disclaimer, the term of this patent is extended or adjusted under 35 U.S.C. 154(b) by 498 days.

(21) Appl. No.: 10/773,719

(22) Filed: Feb. 6, 2004

(65) Prior Publication Data

US 2005/0173829 A1 Aug. 11, 2005

(51) Int. Cl.
*B23P 17/00* (2006.01)
*B29C 33/40* (2006.01)
*A61F 2/60* (2006.01)

(52) U.S. Cl. .............. 29/527.1; 29/402.01; 29/402.09; 29/402.18; 29/527.2; 264/222; 264/223; 623/901

(58) Field of Classification Search ............ 29/402.01, 29/402.09, 402.18, 527.1, 527.2; 623/33, 623/901; 264/223, 222, 220, 225
See application file for complete search history.

(56) References Cited

U.S. PATENT DOCUMENTS

| | | | | |
|---|---|---|---|---|
| 1,351,789 A | * | 9/1920 | Rowley | 264/222 |
| 1,365,424 A | * | 1/1921 | Rowley | 623/37 |
| 3,377,416 A | * | 4/1968 | Kandel | 264/222 |
| 3,520,002 A | * | 7/1970 | Wellington | 623/36 |
| 4,126,924 A | * | 11/1978 | Akins et al. | 29/423 |
| 4,704,129 A | * | 11/1987 | Massey | 623/25 |
| 4,842,608 A | * | 6/1989 | Marx et al. | 623/33 |
| 5,226,918 A | * | 7/1993 | Silagy et al. | 623/27 |
| 5,258,036 A | * | 11/1993 | Edenbaum et al. | 623/33 |
| 5,432,703 A | * | 7/1995 | Clynch et al. | 700/163 |
| 5,571,206 A | * | 11/1996 | Varn | 623/27 |
| 5,718,925 A | * | 2/1998 | Kristinsson et al. | 425/2 |
| 5,827,165 A | * | 10/1998 | Achelpohl et al. | 493/256 |
| 5,888,231 A | * | 3/1999 | Sandvig et al. | 623/36 |
| 5,980,576 A | * | 11/1999 | Graf et al. | 623/33 |
| 6,083,442 A | * | 7/2000 | Gabilly | 264/163 |
| 6,436,149 B1 | * | 8/2002 | Rincoe | 623/47 |
| 6,444,282 B1 | * | 9/2002 | Shirer | 428/35.7 |
| 6,709,617 B2 | * | 3/2004 | Wu | 264/222 |
| 6,991,657 B1 | * | 1/2006 | Price, Jr. | 623/33 |

\* cited by examiner

*Primary Examiner*—Essama Omgba
(74) *Attorney, Agent, or Firm*—Goldizen & Associates; Bradley D. Goldizen (57) ABSTRACT

A method of sizing, resizing or reshaping the interior of a prosthetic device includes placing a lightweight moldable or shape assuming, pliable material that adheres and hardens on the interior sides of a socket of a prosthetic device. An end of a residual limb is placed into the socket causing the moldable material to conform to the shape of the residual limb. The limb is maintained in position for a few minutes in the socket until the moldable material has sufficiently hardened. After hardening, the molded material is dressed down, sanded or feathered to remove any burrs or sharp edges. Low spots or holes may be filled in with more moldable material and the fitting process repeated.

19 Claims, 8 Drawing Sheets

PRIOR ART

PROSTHETIC INTERIOR CASTING PROCESS AND PRODUCT

There are no related applications.

The present invention did not receive federal research and development funding.

FIELD OF THE INVENTION

The present invention generally relates to a method for resizing and reshaping the interior of a socket that accepts a residual limb. More specifically, the invention relates to a method for periodically recreating an accurate interior socket that form fits over a distal end of an amputee or birth defective residual limb.

BACKGROUND OF THE INVENTION

When an amputation occurs or a child is born with a birth defect, the person is sometimes fitted with a prosthetic device that replaces a missing limb or other part of the body. These devices are commonly referred to as prosthesis. They are usually very expensive and come in a variety of shapes and sizes along with differing features. Typical costs associated with designing and producing a prosthetic device exceeds ten thousand U.S. dollars.

In order to better understand the invention at hand, it is necessary to understand the language used when describing certain parts of prosthetic devices.

A socket is the part of the prosthesis that comes in contact with the residual limb. Since a prosthetic device is personalized to a single residual limb, the socket is shaped to receive only a particular residual limb having a certain shape and size. That is to say, most prosthetic devices are produced for a single user and are therefore not mass produced.

Straps or a suspension lock is the portion of the prosthesis that fastens the prosthesis to the residual limb. The suspension lock may include a gel liner, a lock rod and a locking device such as a socket lock. Typically, the locking device is located in the shank of a leg prosthesis.

A lock rod is a pin or stud affixed at an end of the residual limb usually by a gel liner. The lock rod is inserted into a locking device for holding the prosthetic device onto the residual limb. It also provides a means for transmitting axial tension from the distal end wall of a gel liner through a locking mechanism and into the shank portion of the prosthetic device.

A socket lock includes a receptacle and a locking mechanism located below the socket for holding the prosthesis in place. Typically, the socket lock comprises a device that accepts the lock rod and secures it into place. A release allows the user to disengage the locking mechanism such that the prosthetic device can be removed from the residual limb.

A gel liner is a nylon sock for receiving a residual limb. The gel liner may include an integrated end fitting for accepting a lock rod or pin. It may vary in thickness throughout.

A shank is the part of the prosthesis between the knee and foot in a leg prosthesis. It ordinarily comprises metal pipe covered with foam or a hard, hollow tube.

A prosthetist measures or profiles the distal end of the residual limb to create a socket for the prosthesis. Modern advancements now allow many manufacturers to measure an end of the residual limb through the use of laser or other measuring devices.

Over time, many amputees experience shrinking of the residual limb due to reduced swelling and blood flow or muscle atrophy. This causes an inordinate amount of play between the edges of the socket and the residual limb which tends to lead to problems such as blistering or sores being created on the residual limb. To counter these problems, an amputee typically has a new prosthetic device designed and manufactured.

SUMMARY OF THE INVENTION

The process of the present invention ensures a comfortable refitting of a prosthetic limb device to a residual limb of an amputee or any prosthetic limb dependant person.

The present invention is a method for resizing and reshaping the interior of the socket of a prosthetic limb device such that the life of the device may be extended. The method is especially appropriate for individuals who receive donated prosthetic devices to resize and reshape the interior of the used socket for more efficient use. This process reduces costs associated with using and maintaining prosthetic devices by eliminating the need for a new prosthetic device when the size of the residual limb becomes smaller or shrinks. Since the amount of useful life for the prosthetic device is extended, the total amount of replacement costs associated with the prosthetic device is lowered.

An object of the invention is to provide a method of sizing, resizing and reshaping an interior receptacle or socket of a prosthetic device to create an exact complementary socket that receives at least an end of a residual limb.

Another object of the invention is to provide a prosthetic device that includes a socket that may be periodically resized such that it is a definitive socket complementary to an end of the residual limb.

Another object of the invention is to provide a kit for resizing and reshaping the interior socket of a prosthetic device.

A preferable lightweight moldable, curable, socket material in accordance with this invention comprises plastic, fiberglass and epoxy resins and an activator similar to that sold under the brand name Bondo®. However, it is contemplated that other materials may be substituted in the process to achieve the same or similar results. The material used need only be lightweight, moldable, curable and exhibit adhering properties. That is to say, the material used must adequately bond or adhere to a variety of materials used in production of prosthetic devices such as fiberglass, composites, plastic, wood, metal or other such materials that comprise an artificial limb. These moldable curable socket materials include substances soft enough to be molded, yet capable of hardening into a desired fixed form.

In the preferred embodiment, an air space is created by placing a sponge gasket or other suitable material into a bottom of a socket of the prosthetic device. The sponge gasket includes a hole in the center for permitting the locking pin on the tip of the gel liner to reach the pin lock hole at the bottom interior of the socket. The opening in the space creating material or sponge gasket should line up with the pin lock hole. Alternatively, the sponge gasket may be slid over the pin or lock rod before it is inserted into the socket of the prosthetic device. A latex sheath (condom) is pulled over the residual limb which includes the gel liner or a limb sock if a pin lock gel liner is not being used. A layer of lightweight moldable curable material is deposited from a top interior wall of the socket downwards to approximately two-thirds of the way down. In other words, the lightweight moldable curable material is deposited on the upper two-thirds of the interior wall of the socket. The lightweight moldable curable material is prevented from entering the lock pin hole as well as contacting the bottom portion of the socket covered by the sponge gasket. This keeps the lightweight, moldable, curable material from entering the locking mechanism which results in damage to or destruction of the locking mechanism. The sponge also acts as a gasket to keep the residual limb from bottoming out.

After the latex sheath (condom) has been inserted over the gel liner, the socket pin passes through the opening in the space creating material (sponge) and the pin is locked down several clicks. Downward pressure is applied to the distal end of the residual limb to create compression causing the lightweight, moldable, curable material to become formed to the residual limb. Any excess lightweight, curable, moldable molding material that may have overflowed from the top of the socket must be quickly removed from the exterior of the prosthesis.

The above described process may be modified if the prosthetic device is a strap-on or does not include a pin locking mechanism. In this case, the space creating material is slipped into the bottom of the socket, if an air space is desired, and lightweight moldable, curable material is deposited into the socket. This material is compressed using the end of the residual limb. Any excess is removed as mentioned previously.

In the preferred embodiment, Bondo® works well as the lightweight, moldable, curable material described above. The chemical reaction of the hardener with the Bondo® causes the Bondo® to heat up and harden within a few minutes. When the lightweight, curable, moldable material has hardened, the residual limb is removed from the socket. Next, the space creating material (sponge) is removed from the bottom of the socket. The interior of the socket housing now reflects a cast of the end of the residual limb.

This process may be repeated to remove any irregularities in the new interior socket surface caused by bubbles or misapplication of the lightweight, curable, moldable material. Typically in this instance, a thinner direct application of the lightweight, curable moldable material is applied to any irregular areas. However, should the interior surface of the socket include rough edges or raised areas, these areas may be removed by feathering them down with a medium grade sand paper. Lastly, the new interior surface of the socket is sanded with a fine grade sand paper to produce a smooth surface.

In an alternative embodiment, the lightweight curable, moldable material is liquefied and poured into the socket housing around the inserted residual limb. This method may be quicker but overflow and seepage into the locking mechanism is harder to control.

It is contemplated that the lightweight, curable, moldable material may be of any suitable materials that will achieve the formation of a socket that includes the necessary physical characteristics for forming a unique socket and thereafter hardening into a composition that will support the residual limb.

Further objects, features and advantages of the invention will become apparent from a consideration of the following description and the included claims when taken in connection with the previous discussion and the accompanying drawings.

PARTS LIST

1—Prosthetic Device
3—Socket
5—Residual Limb
7—Gel Liner
8—Open end of Gel Liner
9—Lock Rod
10—Reinforced Bottom of Gel Liner
11—Shank
13—Foot
15—Pin Lock Hole
17—Top of Socket
19—Bottom of Socket
21—Lightweight, Moldable, Curable Socket Material
23—Space Creating Material
24—Opening in Space Creating Material
25—Air Space
27—Play Space
29—Latex Sheath
30—Open End of Latex Sheath
31—Interior Wall of Socket
32. Opening in Sheath
33—Top of Socket
35—Bottom of Socket
50—Lock Release Button

DETAILED DESCRIPTION OF THE INVENTION

Figure 1:
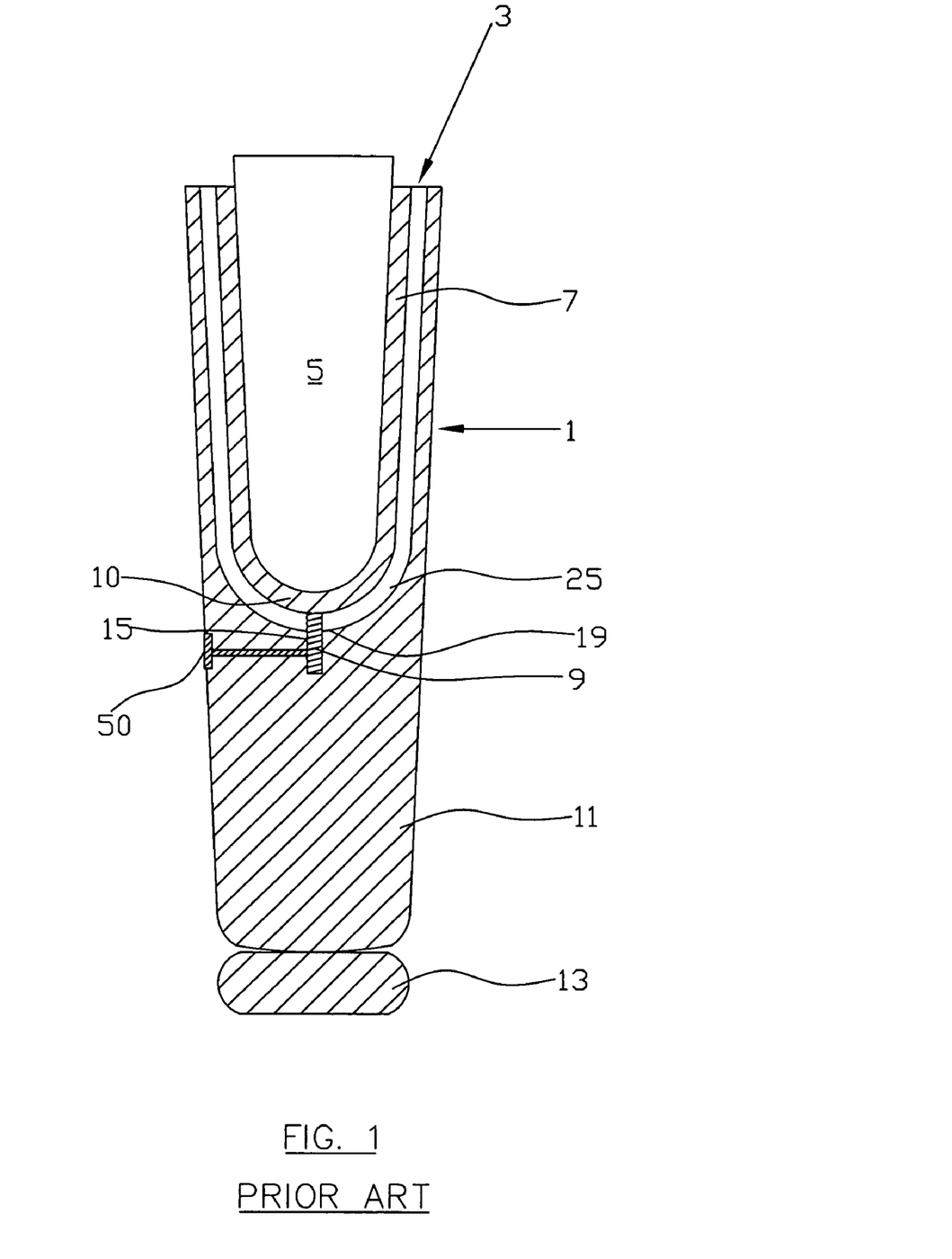
FIG. 1 is a front elevation, section view of a prior art prosthetic limb device.
Figure 2:
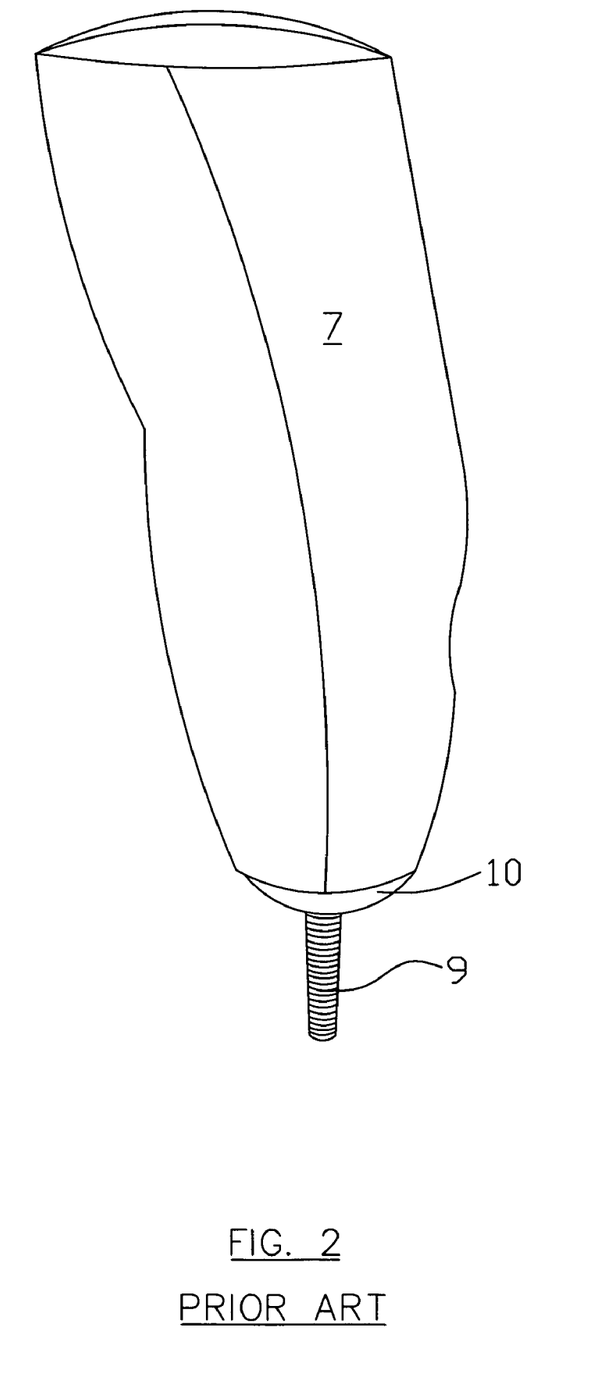
FIG. 2 is a perspective view of a prior art gel liner.

Referring now to FIGS. 1 and 2 that depicts a prosthetic limb device 1 and gel liner 7 attached to a residual limb 5. The prosthetic device 1 is a leg prosthesis that includes a foot 13. The gel liner is worn over the residual limb like a sock. The gel liner 7 includes a lock rod 9 attached to a reinforced bottom 10. Typically, gel liner 7 comprises lycra, nylon or other such material and surrounds the residual limb 5 to provide cushioning and shock absorbing abilities. Thus, the gel liner 7 is part of the suspension that cushions the residual limb 5 during use of the prosthetic device 1.

The amputee pulls the gel liner or rolls it over the residual limb 5 and then pushes both into socket 3. Socket 3 is constructed during that manufacturing process of the prosthetic limb device 1 such that it is uniquely shaped to accommodate the residual limb 5. An air space 25 is provided near the bottom 19 of socket to prevent the distal end of the residual limb 5 from "bottoming out" during ordinary use. Lock pin 9 extends through pin lock hole 15 and into a locking mechanism located in the shank 11. For ease in understanding the invention, the locking mechanism that secures the lock pin 9 is not shown but is represented by lock release button 50.

Figure 3A:
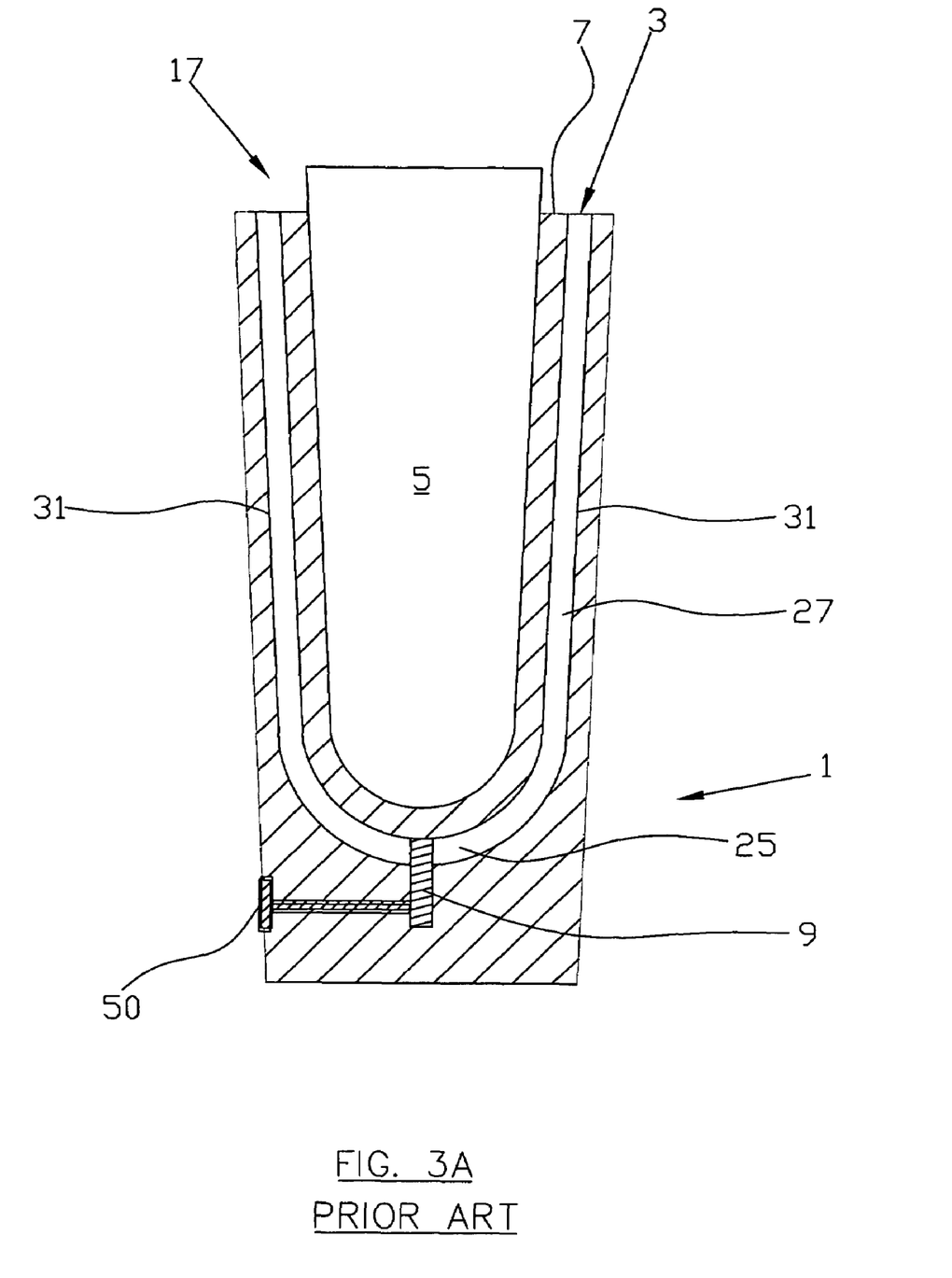
FIG. 3A depicts a section elevation view showing a socket for a prosthetic limb device and a distal end of a residual limb before the present process is undertaken.

FIG. 3A illustrates an example where the residual limb 5 has shrunk such that play represented by air space 27 is created between the interior wall 31 of socket 3. As shown, the air space 27 may extend from the top 17 of socket 3 downwards to air space 25. Thus, socket 3 is incapable of fully supporting the sides of residual limb 5. This situation leads pressure points that are created along the length of the residual limb 5 that extends into socket 3. These pressure points may lead to blisters and sores being created on the residual limb.

Figure 3B:
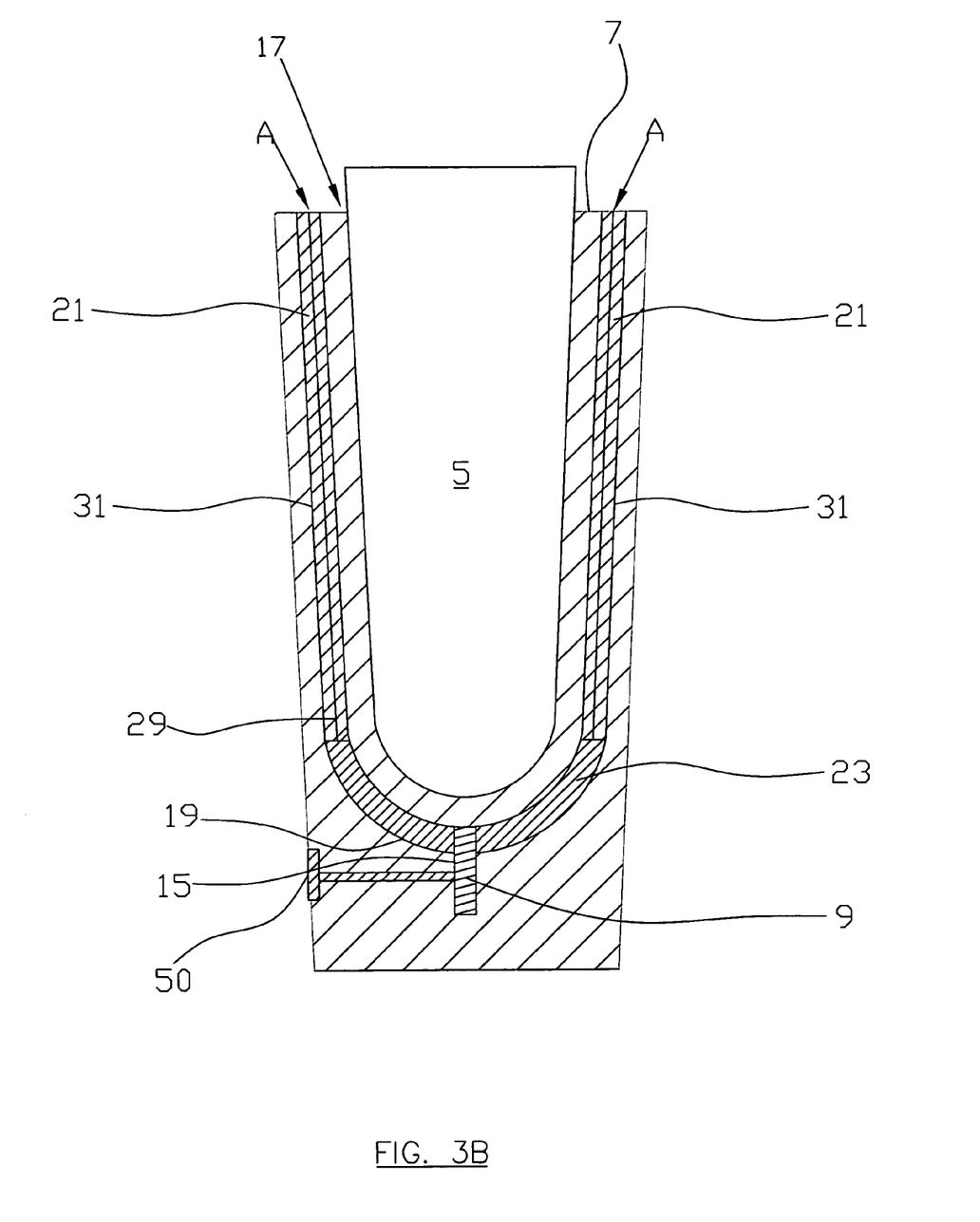
FIG. 3B shows a section elevation view showing a socket for a prosthetic limb device and a distal end of a residual limb while the present process is being undertaken.

This condition can be rectified by carrying out the process steps mentioned above and listed hereinafter. The prosthetic device 1 is removed from the residual limb 5. The interior wall 31 of socket 3 is wiped down and cleaned such that any foreign material is removed. Next, an air space creating material 23, such as a sponge gasket with a center opening, is deposited into a bottom 19 of the socket 3. This material 23 preserves the air space 25 necessary for preventing the residual limb 5 from bottoming out, as mentioned above. The material 23 also prevents the lightweight, moldable, curable socket material 21 from entering the socket lock and fouling it. The opening 24 (shown if FIG. 5B) in the space creating material is positioned such that it is aligned with the pin lock hole 15. A disposable latex sheath (condom) is worn over the residual limb 5 and the gel liner 7 in order to protect the gel liner from adhering to the molding material and to create a smooth surface mold.

Figure 4:
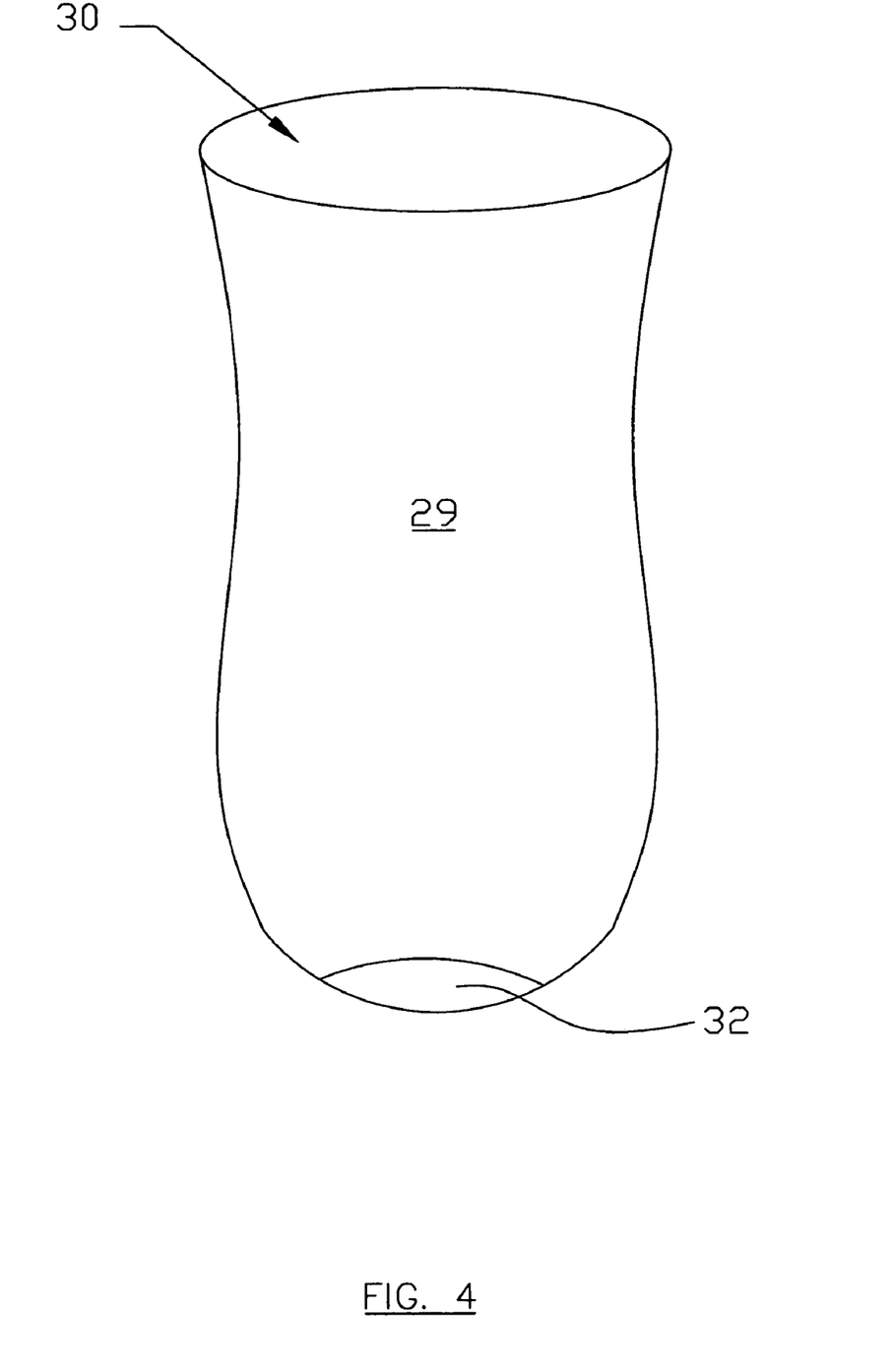
FIG. 4 depicts a latex sheath (condom) for use with the present process.

Next, the distal end of the residual limb 5 wearing the gel liner 7 are inserted into open end 30 of latex sheath (condom) 29. The latex sheath (condom) is worn over these like a sock. The lock rod 9 extends through opening 32. Opening 32 may include a reinforced lip (not shown) which prevents the thin latex material from splitting the sheath (condom) 29 lengthwise as the rod 9 is pushed through opening 32.

A layer of lightweight, moldable, curable socket material 21 is applied from the top to approximately two-thirds way down the interior wall 31 of the socket 3. Care must be taken to prevent the lightweight, moldable, curable socket material 21 from contacting the bottom 19 of the socket 3 to prevent material 21 from entering the pin lock hole 15 and fouling the locking mechanism.

The residual limb 5 wearing the latex sheath (condom) 29, gel liner 7 and sheath 29 are inserted into socket 3. Downward pressure is slowly applied and the lock rod 9 is inserted through opening 24 of the sponge gasket and into the pin lock hole 15. Alternatively, the sponge gasket may be slid over the pin or lock rod before it is inserted into the socket of the prosthetic limb device. The lock rod 9 is locked down several clicks causing the space creating material 23 to be compressed.

Excess lightweight, moldable, curable socket material 21 is compressed upwards towards the top 17 of the socket 3 as shown by arrow A. This excess should be removed quickly before it hardens. In the preferred embodiment, the product registered and sold as Bondo® works well to fulfill this purpose. The chemical reaction of the hardener with the Bondo® causes the Bondo® to heat up and harden within a few minutes.

Figure 3C:
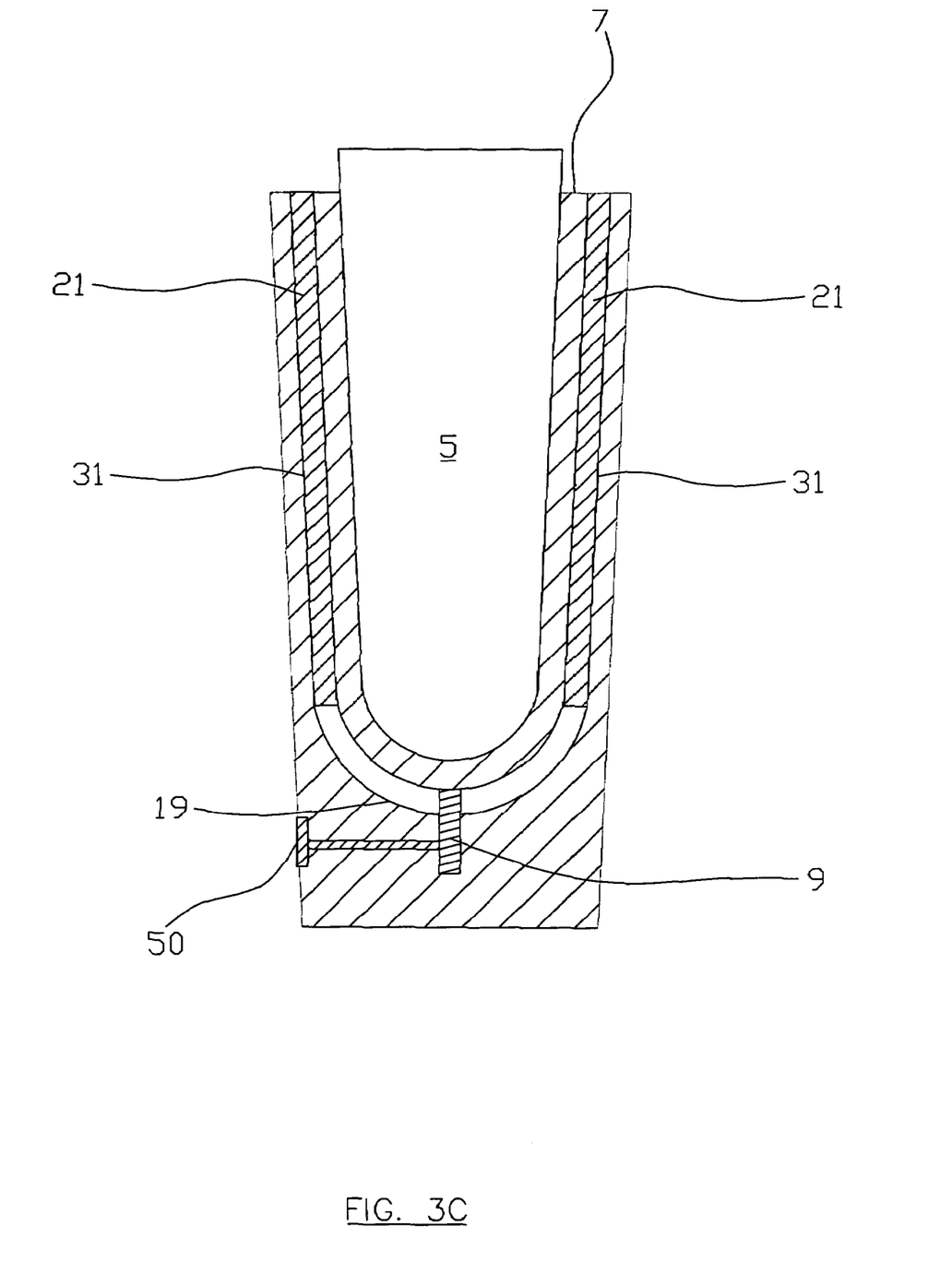
FIG. 3C shows a section elevation view showing the socket and residual limb after the present process has been completed.

When the newly formed socket 3 has hardened, the residual limb 5, gel liner 7 and latex sheath (condom) 29 is pulled out from the socket 3. Next, the space creating material 24 is removed from the bottom 19 of the socket 3. The interior of the socket housing now reflects a cast of the end of the residual limb.

This process may be undertaken again to remove any irregularities in the new cast caused by bubbles or misapplication of the lightweight, moldable, curable socket material 21. Typically in this instance, a thinner or direct application of the lightweight, moldable, curable socket material 21 is applied to irregular areas. However, should the new socket include abrupt edges or raised areas, these areas may be removed by feathering them down with a medium grade sand paper.

Lastly, the interior surface of the new socket is sanded with a fine grade sand paper to produce a smooth surface.

In an alternative embodiment, the lightweight pliable, molding material is liquefied and poured into the socket around the pre-inserted residual limb after the space creating material has been deposited into the socket and with the latex sheath covering the gel liner and residual limb. This mode of application is harder to control.

Figure 5A:
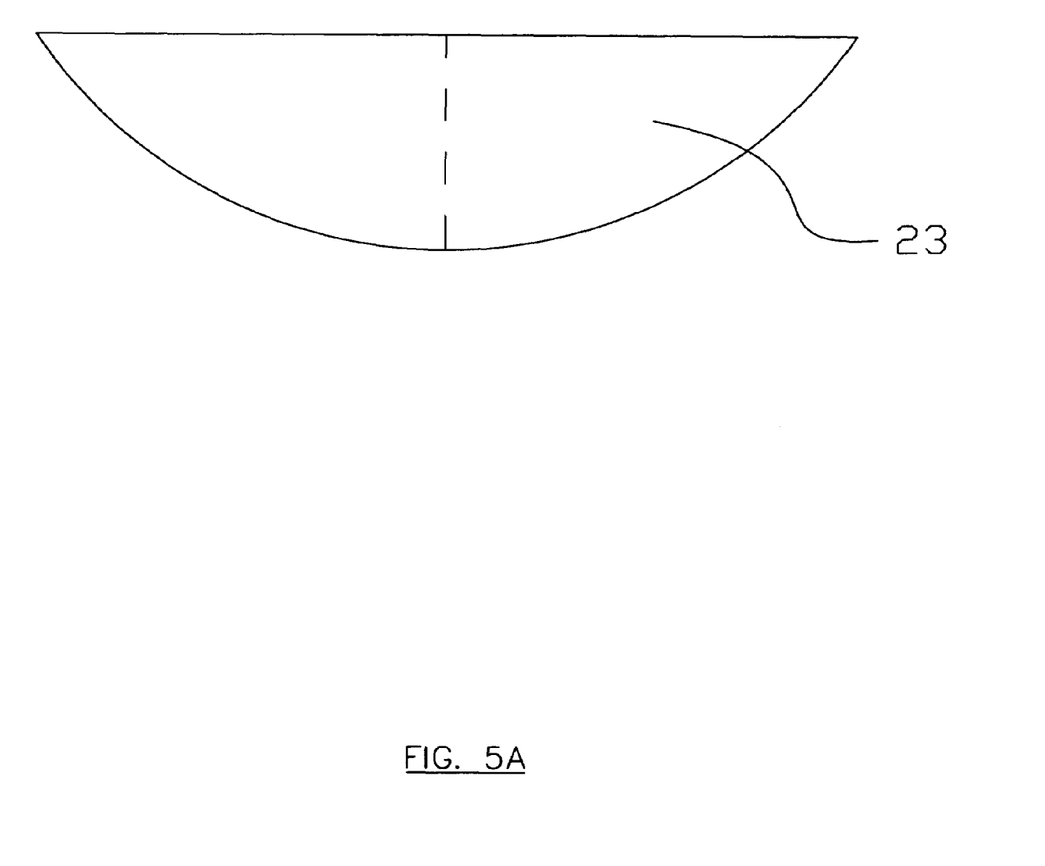
FIG. 5A illustrates a side view of a space creating device
Figure 5B:
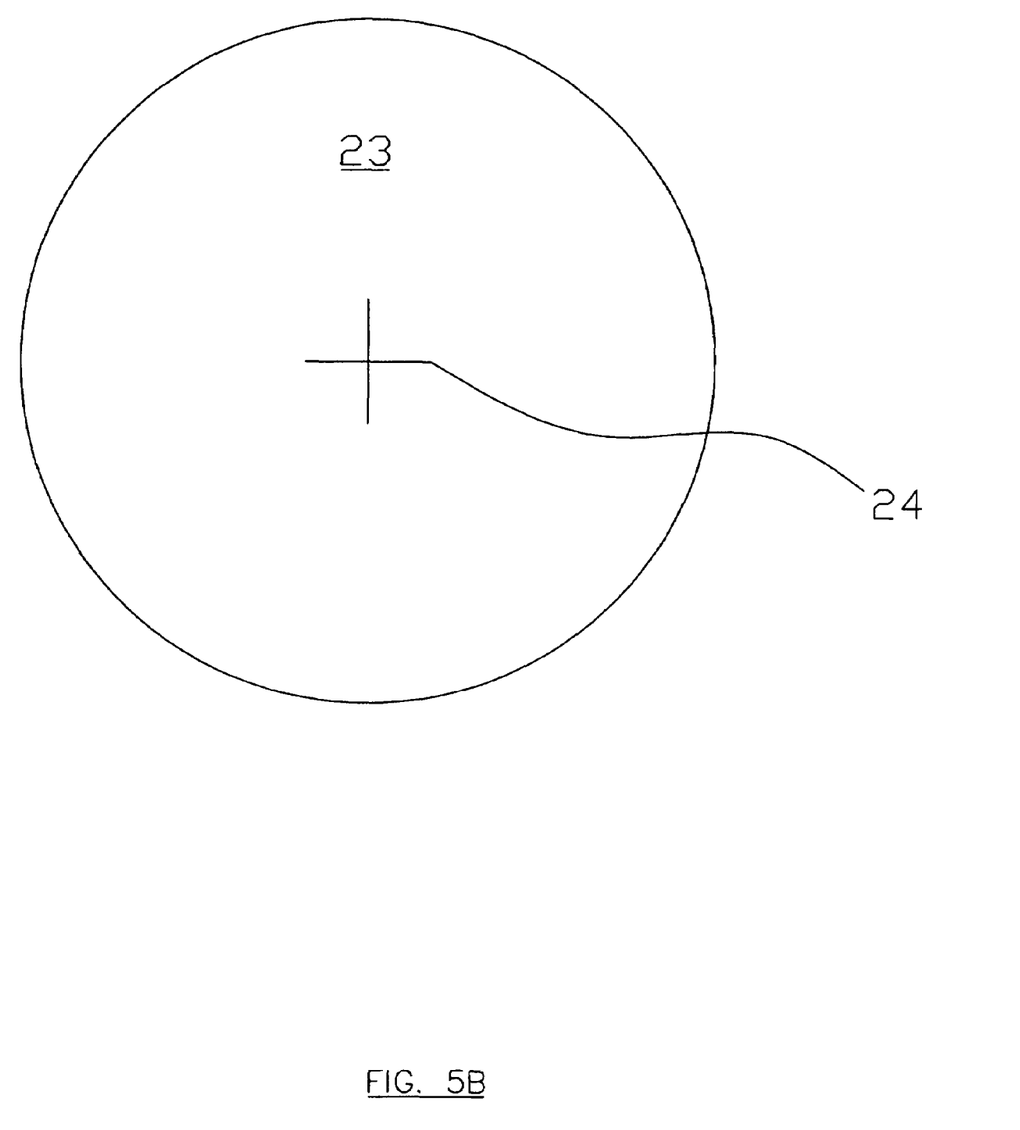
FIG. 5B shows an overhead view of the space creating device.

FIG. 5 shows the preferred shape of the space creating material 23. The material 23 is typically bowl-shaped sponge gasket and having an opening or slits 24 through which lock rod 9 may pass.

It is to be understood that the invention is not limited to the exact steps listed and described above. Various changes, modifications and additional steps may be made or added without departing from the spirit and the scope of the invention as defined in the following claims.

This process becomes applicable when an amputee's or handicapped person's residual limb shrinks or changes its shape after its original fitting. It eliminates the only alternative that presently exists of having to create a new expensive socket. This process is extremely relevant for refitting donated used prostheses to new recipients.

I claim:

1. A process for reshaping or refitting an interior of a socket of a prosthetic device comprising the steps of:
    filling at least a portion of a socket of a prosthetic device with a moldable curable material;
    placing a latex sheath over an end of a residual limb;
    placing a space creating material between a bottom of the socket and the latex sheath;
    inserting the sheath covered residual limb into said socket filled with the moldable curable material; and
    removing said residual limb from the socket filled with moldable curable material after said moldable curable material has assumed a shape of the end of the residual limb to create a new socket having a substantially complementary shape of the end of the residual limb.

2. The process of claim 1 wherein said step of inserting the sheath covered residual limb further comprises applying downward pressure to a distal end of the residual limb to create compression that causes excess moldable curable material to be forced upward and downward along the interior side of the socket.

3. The process of claim 1 further comprising removing excess moldable curable material from the exterior of the prosthetic device.

4. The process of claim 1 further comprising placing a space creating material at a bottom of a socket in a prosthetic device.

5. The process of claim 4 further comprising inserting a socket pin of a gel liner into an opening in the space creating material before inserting the space creating material into the socket.

6. The process of claim 4 further comprising passing a socket pin of a gel liner through an opening in the space creating material.

7. The process of claim 1 further comprising depositing moldable curable material onto an exterior surface of the sheath before inserting the sheath covered residual limb into said socket.

8. The process of claim 1 further comprising removing irregular areas in a new socket by repeating the process by applying a thin application of moldable curable material to the interior of the socket.

9. The process of claim 8 wherein removing said irregular areas in the new socket comprises sanding down the irregular areas.

10. A process that reduces costs associated with maintaining prosthetic devices, the process extends the useful life of a prosthetic device by eliminating the need for a new prosthetic device when a size of an end of a residual limb shrinks, the process includes a method for reshaping or refitting an interior of a socket of a prosthetic device comprising:

depositing a moldable curable material into an interior of a socket of a prosthetic device;

covering an end of a residual limb with a sheath;

inserting the end of the residual limb covered by the sheath into the socket of the prosthetic device to cause the moldable curable material to conform to a shape of the end of the residual limb; and, removing said residual limb from the socket after said moldable curable material has assumed the shape of the end of the residual limb to create a socket having a substantially complementary shape of the end of the residual limb.

11. The process of claim 10 wherein said inserting the sheath covered residual limb further comprises applying downward pressure to a distal end of the residual limb to create compression that causes excess moldable curable material to be forced upward and downward along the interior wall of the socket.

12. The process of claim 10 further comprising removing excess moldable curable material from the exterior of the prosthetic device.

13. The process of claim 10 further comprising placing a space creating material at the bottom of a socket in the prosthetic device.

14. The process of claim 13 further comprising inserting a socket pin of a gel liner into an opening in the space creating material before inserting the space creating material into the socket.

15. The process of claim 13 further comprising passing a socket pin of a gel liner through an opening in the space creating material.

16. The process of claim 13 further comprising depositing moldable curable material onto an exterior surface of the sheath before inserting the sheath covered residual limb into said socket.

17. The process of claim 10 further comprising removing irregular raised areas in a new socket.

18. The process of claim 17 wherein removing said irregular raised areas in the new socket comprises sanding down the irregular raised areas.

19. A process for shaping an interior of a socket of a prosthetic device comprising the steps of:

placing a latex sheath over an end of a residual limb;

deposited moldable curable material onto an exterior surface of said latex sheath;

placing a space creating material between a bottom of the socket and the latex sheath;

inserting the sheath covered residual limb into said socket such that said moldable curable material fills the socket; and removing said residual limb from the socket filled with moldable curable material after said moldable curable material has assumed a shape of the end of the residual limb to create a new socket having a substantially complementary shape of the end of the residual limb.

* * * * *